United States Patent
Dicke

(10) Patent No.: US 9,139,804 B2
(45) Date of Patent: Sep. 22, 2015

(54) INSERT FOR CELL CULTURES

(75) Inventor: Nikolas Dicke, Einbeck (DE)

(73) Assignee: Sabeu Kunststoffwerk Northeim GmbH, Northeim (DE)

(*) Notice: Subject to any disclaimer, the term of this patent is extended or adjusted under 35 U.S.C. 154(b) by 304 days.

(21) Appl. No.: 13/356,021

(22) Filed: Jan. 23, 2012

(65) Prior Publication Data

US 2012/0214226 A1 Aug. 23, 2012

Related U.S. Application Data

(60) Provisional application No. 61/448,306, filed on Mar. 2, 2011.

(30) Foreign Application Priority Data

Feb. 22, 2011 (DE) ............... 20 2011 003 049 U

(51) Int. Cl.
*C12M 3/00* (2006.01)
*C12M 1/00* (2006.01)
*C12M 1/12* (2006.01)

(52) U.S. Cl.
CPC .................. *C12M 25/04* (2013.01)

(58) Field of Classification Search
CPC ............... C12M 23/24; C12M 23/10
See application file for complete search history.

(56) References Cited

U.S. PATENT DOCUMENTS

| | | | | |
|---|---|---|---|---|
| 4,871,674 A | * | 10/1989 | Matsui et al. | 435/297.5 |
| 5,272,083 A | * | 12/1993 | Butz et al. | 435/401 |
| 5,395,006 A | * | 3/1995 | Verma | 220/371 |
| 5,801,055 A | * | 9/1998 | Henderson | 435/297.5 |
| 7,598,076 B2 | * | 10/2009 | Wedell et al. | 435/297.5 |
| 2008/0076170 A1 | * | 3/2008 | Annala et al. | 435/297.4 |

* cited by examiner

*Primary Examiner* — Nathan Bowers
(74) *Attorney, Agent, or Firm* — Brinks Gilson & Lione

(57) ABSTRACT

An insert for cell cultures has a hollow housing (1) of a cylinder-like shape, with an upper, in particular circular, opening (2) and a membrane-like base located opposite the opening (2). On the peripheral opening edge (6) outward protruding support arms (5) are spaced apart from one another. The housing (1) has on its outer peripheral surface (12), between at least two support arms (5), a flattened region (11) extending from the opening edge (6) in the direction of the base (3), so that in a plane perpendicular to the central longitudinal axis (Y) of the housing (1) in the region of the flattened region (11) there is a radial clearance of the peripheral surface (12) relative to the longitudinal axis (Y) which is smaller than the radial clearance and/or outer radius of the peripheral surface (12) in the non-flattened region of the peripheral surface (12).

12 Claims, 3 Drawing Sheets

INSERT FOR CELL CULTURES

CROSS REFERENCE TO RELATED APPLICATIONS

This application claims priority to Provisional Patent Application No. 61/448,306, filed Mar. 2, 2011, and to German Utility Model No. 20 2011 003 049.0, filed Feb. 22, 2011.

TECHNICAL FIELD OF THE INVENTION

The present invention relates to an insert for cell cultures, with a hollow housing with a cylinder-like shape, having an upper opening on one axial side and a membrane-like base located opposite the opening, as well as radially outward protruding support arms spaced apart from one another and distributed on the peripheral opening edge surrounding the upper opening.

BACKGROUND OF THE INVENTION

A cell culture insert of the above-mentioned kind is known from DE 102 40 787 A1. In the cell culture insert according to that reference, the support arms and spacers dedicated to the support arms are distributed along the perimeter of the cell culture insert and configured with different lengths on the sides. The eccentric mounting owing to the differently configured support arms and spacers thus increases the size of a feeding window located between the cell culture insert and a surrounding wall of a multiwell plate into which a pipette can be inserted. This design of the cell culture insert has disadvantages in that these inserts are not located in the center of a receptacle for a multiwell plate. Consequently, positioning difficulties arise during automatic filling of the inserts.

SUMMARY OF THE INVENTION

The underlying object of the present invention based on a generic insert is to provide an enlargement of the space between the insert and an opening wall of a well of a multiwell plate for inserting a pipette and to simplify a centric arrangement of the insert in the well.

According to the present invention, this object is attained in that on its outer peripheral surface, the housing has a flattened region extending from the opening edge in the direction of the base between at least two support arms, so that, in a plane perpendicular to the central longitudinal axis of the housing in the flattened region, the radial clearance of the peripheral surface relative to the central longitudinal axis flattened region is smaller than the respective radial clearance of the peripheral surface in the non-flattened region of the peripheral surface. Another way to describe this is that, in planes intersecting the flattened region perpendicular to the longitudinal axis Y, the unflattened peripheral surface of the housing defines a circle centered at longitudinal axis Y, and the points along the flattened region lie inside the circle. In this connection, it is advantageous if three support arms mutually offset by 120° are provided, and in particular if such a flattened region extending from the opening edge in the direction of the base is provided between all support arms. The flattened region can also be formed by a flat wall section of the housing so that there is also a flattened region on the inner peripheral surface of the housing. Due to the flattened regions at the perimeter of the peripheral surface, the distance between the insert and the inner wall of the opening in the well is increased so that the insertion of a pipette into this area is simplified, and the centric mounting of the insert in the well is ensured. For this purpose, all the support arms have the same radial length in particular, the support arms preferably having ribs at their undersides facing the base that extend in the direction of the base and taper toward the peripheral surface, whose rib edges pointing away from the peripheral surface run at an acute angle α enclosed by the peripheral surface and the respective rib edge. Advantageously, the individual ribs thus have a triangular shape, two mutually parallel ribs being in particular configured below each support arm, the ribs being parallel to the radial center line of the support arms. When a pipette is inserted into the space between the insert according to the present invention and the inner wall of a well, the pipette displaces the insert out of the well in the upward direction. The embodiment of the ribs according to the present invention thus reduces or to a large extent prevents wobbling and lateral tilting of the insert during such upward movements, namely as a result of the double contact surfaces created by both parallel ribs.

Further advantageous embodiments of the invention will be explained in more detail with reference to the exemplary embodiments shown in the attached drawings.

DETAILED DESCRIPTION OF THE DRAWINGS

Figure 1:
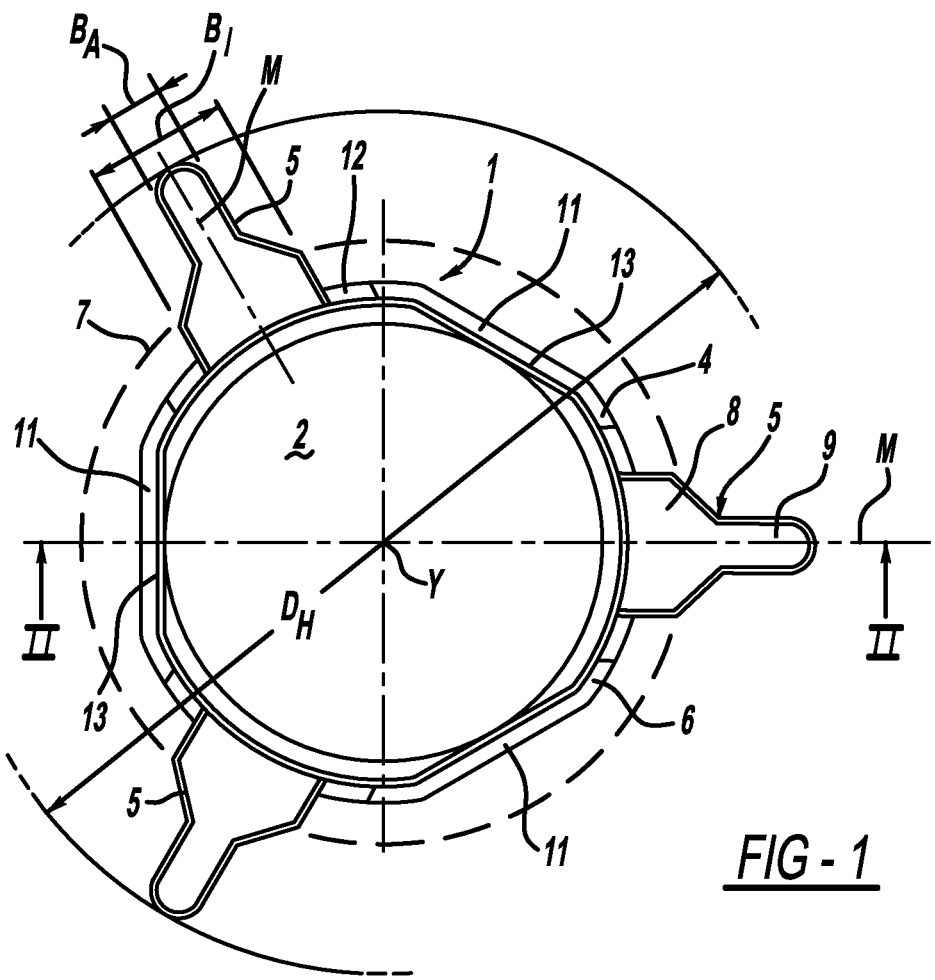
FIG. 1 shows a top view of an inventive insert in a well of a multiwell plate.

The following description of exemplary embodiments serves purely illustrative purposes and is not intended to limit the scope of the present invention. Similar or functionally equivalent parts and components of the insert according to the present invention are provided with the same reference numerals in the different figures.

As is apparent from FIGS. 1 to 4, an insert for cell cultures according to the present invention consists of a hollow housing 1 having a cylinder-like shape. This housing 1 has an upper, in particular circular opening 2 and a base 3 configured as a membrane located opposite the opening 2. The outer diameter of the opening 2 is preferably greater than the outer diameter of the base 3, so that a cross-sectional profile of the housing tapering toward the base results which is perpendicular to the longitudinal axis Y of the housing 1. But it is also within the scope of the invention if the outer diameter of the opening 2 and the outer diameter of the base 3 are the same size, or the outer diameter of the base 3 is greater than the outer diameter of the opening 2. It is likewise within the scope of the invention if the opening 2 and the base 3 are not circular. The opening 2 is surrounded by an edge 4 having mutually distanced support arms 5 extending outward from the periphery of the opening edge. These support arms 5 have a center line M which extends radially from the longitudinal axis Y. The support arms 5 are shaped mirror-symmetrically relative to the center line M and have a radial length such that they rest on a peripheral edge 7 of a well in the fitted state of the insert in the well. The well is a cavity into which the insert 1 is placed during use and which is filled with nutrients for growing the cell culture in insert 1. The peripheral edge 7 of the well is shown as dashed lines in FIG. 1. Three support arms 5 mutually offset by 120° are advantageously provided. The support arms 5 consist of two arm sections 8, 9, namely one radially inner section 8 and one radially outer section 9. In this connection, the radially outer section 9 has a lesser width than the radially inner section 8.

According to the present invention, on its outer peripheral surface between two respective support arms 5, the housing 1 has a flattened region 11 that extends from the edge 4 of the opening 2 in the direction of the base 3, so that in planes perpendicular to the longitudinal axis, points on the flattened region 11 are at a closer radial distance from central longitudinal axis Y of the housing 1 than the radial distance of the peripheral surface 12 of the housing 1 in the non-flattened region of the peripheral surface 12. Another way to describe this is that, in every plane intersecting the flattened region 11 perpendicular to the longitudinal axis Y, the unflattened peripheral surface 12 defines a circle centered at longitudinal axis Y, and the points along the flattened region lie inside the circle. The peripheral surface is identified in the figures with reference number 12. Since three support arms 5 are present in the illustrated embodiment, three flattened regions 11 are also present on the peripheral surface 12 of the housing 1, which are mutually offset by 120°. As is evident from FIGS. 1 to 6, the flattened region 11 can be formed by a planar wall section 13 of the housing 1, so that a flattened region 14 is also present at the inner peripheral surface 15 of the housing 1; see FIG. 2.

Figure 2:
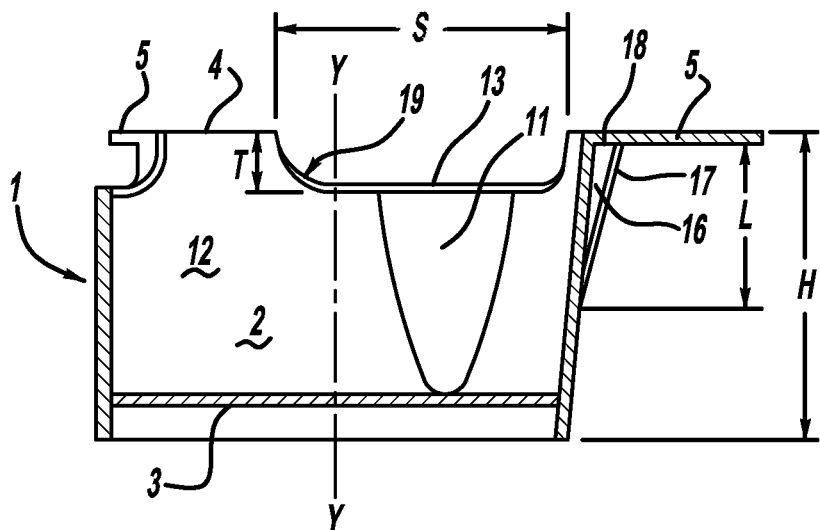
FIG. 2 shows a cross-sectional view taken along the II-II line in FIG. 1.
Figure 3:
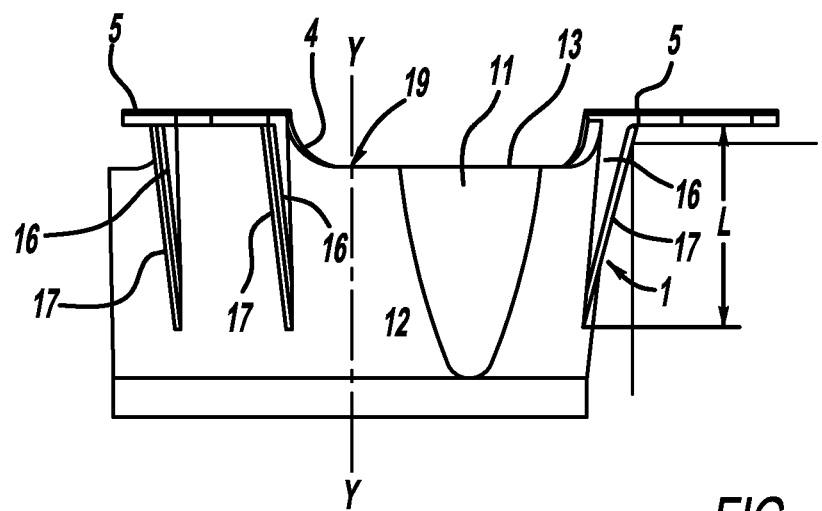
FIG. 3 shows a side view of an inventive insert according to FIG. 1.
Figure 4:
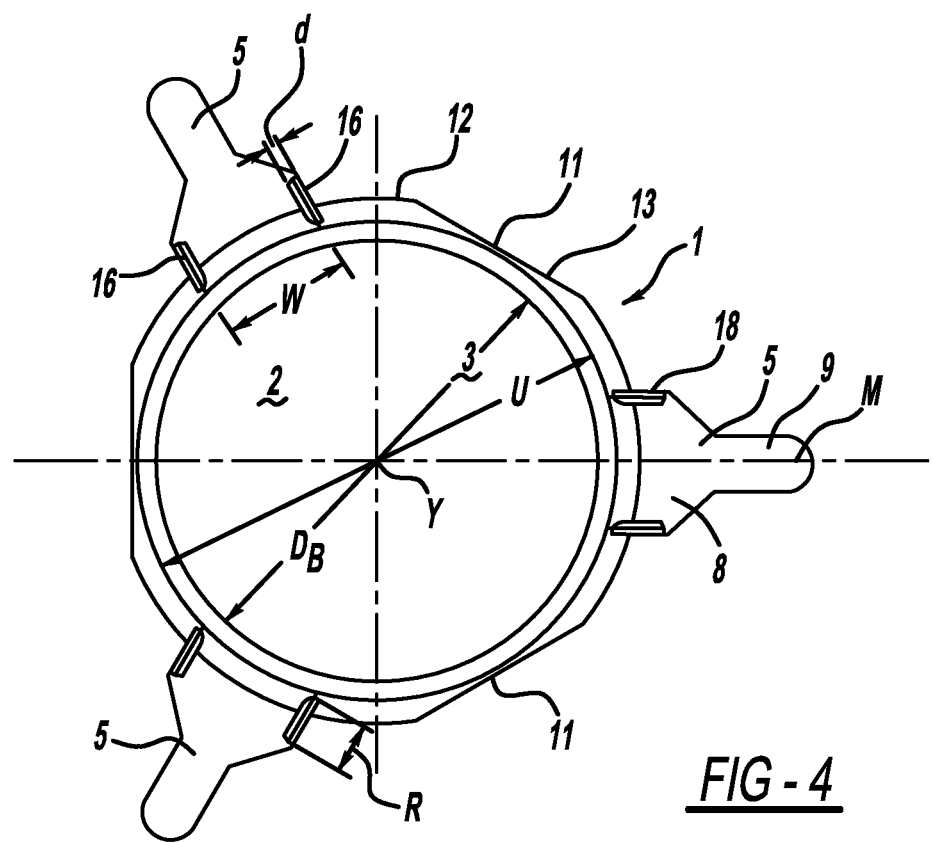
FIG. 4 shows a bottom view of an insert according to FIG. 1.

Furthermore, the invention provides that on their underside facing the base 3, the support arms 5 have ribs 16 which extend from the underside in the direction of the base 3 and have ribs 16 ending at the peripheral surface 12 whose rib edges 17 pointing away from the peripheral surface 12 forms an acute angle enclosed by the peripheral surface 12 and the rib edge 17 (see FIGS. 2 and 3). Advantageously, two mutually parallel ribs 16 are formed under each support arm 5, the ribs 16 extending parallel to the radial center line M of the support arms 5. In this connection, the ribs 16—as is apparent from FIGS. 2 and 3—have a triangular perimeter. As is in particular apparent from FIG. 4, the width W of the radially inner section 8 of the support arms 5 is equal to the outer clearance of the ribs 16 located under each support arm 5, and the radial length R of the radially inner section 8 corresponds to the radial length of the lateral edge 18 of the ribs 16 resting on the support arm 5. The radial length R of the radially inner section 8 is selected such that the insert according to the present invention is positioned centrically in the opening surrounded by the peripheral edge 7 of the well, so that the radial length of the rib is selected such that in the fitted state of the housing 1 according to the present invention the rib 16 rests with its upper end on the inner side of the well paired with the housing 1.

It is furthermore evident that the opening edge 6 of the housing 1 has an axial recess 19 between the support arms 5 in the region of the upper opening 2. Accordingly, there are three recesses 19 mutually offset by 120° on the perimeter of the opening 2 of the exemplary embodiments. The depth T (see FIG. 2) of the recesses 19, measured at the top side of the support arms 5, is in particular 2.8 to 3 mm. The length S (see FIG. 2) of the recesses 19, measured at the peripheral surface 12 of the housing 1 is in particular 5.4 to 9.3 mm. The depth T of the axial recesses 19 is relatively greater for greater diameters of the opening 2, and the length S of the axial recesses 19 is relatively smaller for greater diameters of the opening 2.

Figure 5:
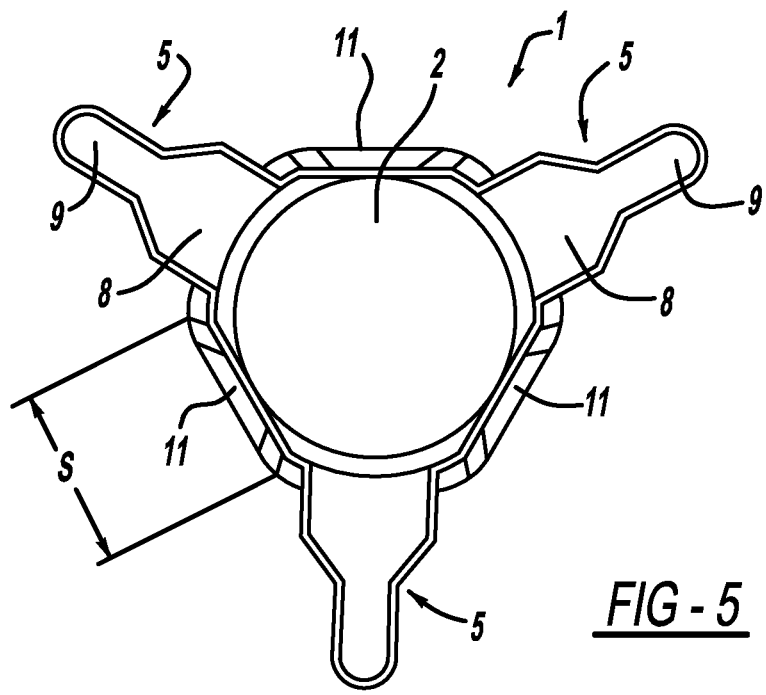
FIG. 5 shows a top view of an insert according to a second illustrative embodiment of the present invention with a reduced diameter compared to the insert according to FIG. 1.
Figure 6:
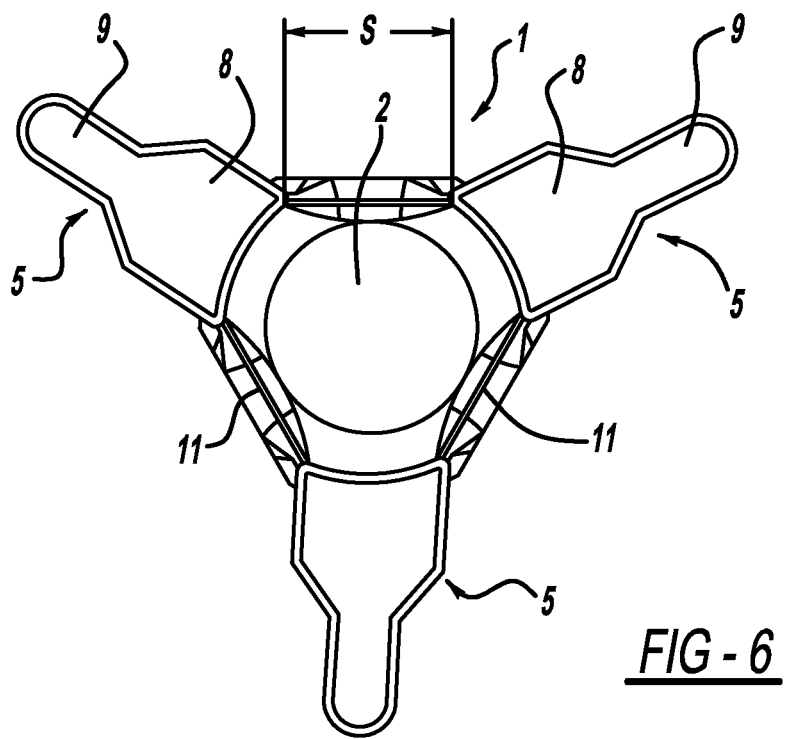
FIG. 6 shows a top view of an insert according to a third illustrative embodiment of the present invention with a further reduced outside diameter of the housing in comparison with the insert in FIG. 5.

FIGS. 1, 5 and 6 show housings 1 of different sizes according to the present invention. In housing 1 according to FIG. 1, an enveloping circle around the outer ends of the support arms 5 has a diameter $D_H$ of 47 mm, the width $B_I$ of the radially inner section 8 of each support arm 5 is 7.6 mm, and the width $B_A$ of the radially outer section 9 of each support arm 5 is 3.0 mm. The base has a diameter $D_B$ of 24 mm (see FIG. 4). The wall thickness d of the ribs 16 is 0.6 mm. The outer diameter U of the peripheral surface 12 is 28.5 mm in the region below the support arms 5. The height H of housing 1 is 16.3 mm and the axial length L of the ribs 16 is 11.82 mm.

The corresponding dimensions of the exemplary embodiments according to FIGS. 5 and 6 are shown in the table below.

| [mm] | $D_H$ | $B_I$ | $B_A$ | $D_B$ | d | U | H | L |
| --- | --- | --- | --- | --- | --- | --- | --- | --- |
| FIG. 5 | 32.37 | 6.10 | 3.00 | 12.00 | 0.60 | 16.43 | 16.30 | 10.89 |
| FIG. 6 | 25.11 | 4.60 | 2.00 | 6.54 | 0.60 | 10.97 | 16.30 | 9.94 |

As is in particular apparent from FIGS. 1, 5, 6, the peripheral length S of the recesses 19 with respect to the peripheral distance between the support arms 5 is variable depending on the size of the housing 1. By way of example, in the embodiment according to FIG. 1 the peripheral length S of the recess 19 is 40 to 60% of the peripheral distance between the support arms 5, whereas in the embodiment according to FIG. 5, the peripheral length of the recess 19 is 60 to 80% of the peripheral clearance of the support arms 5. In FIG. 6 the peripheral length of the recess 19 encompasses the entire peripheral clearance of the support arms 5.

With the exception of the membrane-like base 3, the housing 1 base 3 is advantageously configured as a one-piece injection molded plastic part. The base 3 configured as a membrane is likewise produced as a molded plastic part and is subsequently attached to the housing 1 either by adhesion or welding. It is likewise possible to integrate the base 3 placed in the injection molding tool during the injection molding process in the housing 1 by insert molding.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:
1. An insert for cell cultures, comprising:
a hollow cylinder-like housing having a central axis and a first axial end and a second axial end and having an upper opening with an opening edge at the first axial end and a membrane-like base near the second axial end;

three outward protruding support arms spaced apart from one another by 120° and distributed on a peripheral edge surrounding the opening, each of the three support arms having two ribs extending parallel to each other and to the central axis on an underside facing toward the second axial end and configured to facilitate an upward displacement of the insert during pipetting, each of the support arms having a width adjacent the peripheral edge that is equal to an outer clearance of the two ribs located under the support arm;

the housing having an outer peripheral surface with three flattened regions in an angular area between respective two of the support arms, the three flattened regions extending from the opening edge toward the base, such that in planes extending through the at least one flattened region and perpendicular to the central axis, the outer peripheral surface defines a circle centered at the central axis, and all points of the three flattened regions lie inside the circle.

2. The insert according to claim 1, further comprising that the housing has an inner peripheral surface and that each of the three flattened regions is formed by a flat wall section of the housing and the inner peripheral surface is flattened by the at least one flattened region.

3. The insert according to claim 1, further comprising that all support arms have an equal radial length.

4. The insert according to claim 1, further comprising that the outer peripheral surface has a greater diameter proximate the first axial end than proximate the second axial end.

5. The insert according to claim 1, further comprising that each of the two ribs is tapered toward the outer peripheral surface and has a side edge extending at an acute angle relative to the outer peripheral surface.

6. The insert according to claim 1, wherein each of the three support arms comprises a radially inner section and a radially outer section, the radially outer section having a smaller width in circumferential direction of the housing than the radially inner section.

7. The insert according to claim 6, wherein the width of the radially inner section of each support arm connects the ribs associated with the support arm and wherein the radially inner section extends radially over a distance that covers the ribs.

8. The insert according to claim 1, wherein the opening edge of the housing has three axial recesses, one of the recesses being arranged between each pair of adjacent support arms of the three support arms.

9. The insert according to claim 1, further comprising that the housing and the base are each designed as injection molded plastic parts and the base is secured in the housing by gluing or welding.

10. The insert according to claim 1, wherein the first and second axial ends have the same diameter.

11. The insert according to claim 1, wherein the first and second axial ends have different diameters.

12. An insert for cell cultures, comprising:
a hollow cylinder-like housing having a central axis and a first axial end and a second axial end and having an upper opening with an opening edge at the first axial end and a membrane-like base near the second axial end;
three outward protruding support arms spaced apart from one another by 120° and distributed on a peripheral edge surrounding the opening, each of the three support arms having a radially inner section, a radially outer section having a width narrower than the radially inner section, and two ribs facing toward the second axial end and extending parallel to each other and to the central axis on an underside of the support arms, the two ribs configured to facilitate an upward displacement of the insert during pipetting, the ribs having a greater distance from each other than the width of the radially outer section;
the housing having an outer peripheral surface with three flattened regions in an angular area between respective two of the support arms, the three flattened regions extending from the opening edge toward the base, such that in planes extending through the at least one flattened region and perpendicular to the central axis, the outer peripheral surface defines a circle centered at the central axis, and all points of the three flattened regions lie inside the circle.

\* \* \* \* \*